United States Patent [19]
Lin et al.

[11] Patent Number: 4,876,398
[45] Date of Patent: Oct. 24, 1989

[54] PREPARATION OF ORTHO-ALKYLATED PHENOLS IN THE PRESENCE OF A CATALYST PREPARED BY CO-PRECIPITATION PROCESS

[75] Inventors: Trong-Goang Lin, Hsinchu; Ling-Wen Ho; An-Nan Ko, both of Taipei; Yeong-Ju Perng, Miaoli, all of Taiwan

[73] Assignee: China Petrochemical Development Corporation, Taipei, Taiwan

[21] Appl. No.: 206,834

[22] Filed: Jun. 10, 1988

[51] Int. Cl.$^4$ .................. C07C 37/16; C07C 37/00
[52] U.S. Cl. .................................................. 568/804
[58] Field of Search ........................................ 568/804

[56] References Cited
U.S. PATENT DOCUMENTS

| | | | |
|---|---|---|---|
| 3,972,836 | 8/1976 | Van Sorge | 568/804 |
| 3,974,229 | 8/1976 | Van Sorge | 568/804 |
| 4,528,407 | 7/1985 | Smith et al. | 568/804 |
| 4,547,480 | 10/1985 | Bennett et al. | 568/804 |
| 4,590,307 | 5/1986 | Bennett et al. | 568/804 |
| 4,661,658 | 4/1987 | Battista et al. | 568/804 |
| 4,677,089 | 6/1987 | Bennett et al. | 568/804 |

Primary Examiner—Werren B. Lone
Attorney, Agent, or Firm—Cushman, Darby & Cushman

[57] ABSTRACT

A process for preparing an ortho-alkylated phenol is conducted by a vapor phase catalytic reaction at 200°–500° C. by reacting a vapor phenol compound selected from phenol, ortho-cresol and a mixture of phenol mixed with ortho-cresol with a vapor alcohol selected from methanol, in the presence of a catalyst containing magnesium oxide and manganese oxide, wherein the catalyst is prepared by treating an alkali in an aqueous solution having soluble magnesium ion and manganese ion to obtain coprecipitate of magnesium and manganese salt with respect to the alkali added, and the coprecipitate is then filtered, water-washed and calcined at 250°–600° C. for 1–4 hours for forming the catalyst consisting of magnesium oxide and manganese oxide having an atomic ratio of Mg/Mn of 1:1 to 100:1.

9 Claims, No Drawings

PREPARATION OF ORTHO-ALKYLATED PHENOLS IN THE PRESENCE OF A CATALYST PREPARED BY CO-PRECIPITATION PROCESS

BACKGROUND OF THE INVENTION

Bernardus J. Van Sorge disclosed a catalyst for the preparation of ortho-alkylated phenols of U.S. Pat. No. 3,972,836 in which the catalyst is made by blending mixture of magnesium oxide and a manganese oxide with about an equal amount of water, molding the blend to shape, drying the shaped blend, and heating at the calcination temperature to form the catalyst. Van Sorge also disclosed a preparation of ortho-alkylated phenols in his U.S. Pat. No. 3,974,229 by conducting the alkylation reaction in the presence of a catalyst prepared by physically blending a mixture of magnesium oxide with 1-15% by weight of manganese oxide with water, molding and heating to form the catalyst. Hence, the two patents disclosed by Van Sorge are substantially the same for teaching the preparation of a catalyst adapted for preparing ortho-alkylated phenols by blending magnesium oxide and manganese oxide, which however still results in a poor yield of 2,6-dimethyl phenol, for instance, the 2,6-xylenol distribution (wt. %) being only 50.2% when the reaction is performed at a temperature of 480° C. for 400 hours as shown in Example 3 (Run 3a), showing an activity of the catalyst being not so satisfactory.

The present inventors have found the drawback of Van Sorge's process and invented the present process for preparing a catalyst for ortho-alkylation of a phenol compound by improving the catalyst activity and product yield over the Van Sorge's process.

SUMMARY OF THE INVENTION

One object of the present invention is to provide a process for preparing ortho-alkylated phenols in the presence of a catalyst prepared by treating an alkali in an aqueous solution of magnesium and manganese ions to obtain a co-precipitation of magnesium and manganese salts with respect to the added alkali, which is then filtered, washed, dried, shaped and calcined to form the catalyst having a higher activity and longer life, for reducing the reaction temperature and product yield of the alkylated phenols.

Another object of the present invention is to provide a catalyst prepared as aforementioned being further impregnated in an aqueous solution of an alkali metal salt and then calcined at a high temperature to form a layer of an oxide of alkali metal on the catalyst to prolong the catalyst life.

DETAILED DESCRIPTION

The present invention comprises a preparation of orthoalkylated phenols by reacting a phenol compound and a alcohol at a temperature from 200° C. -500° C. in the presence of a catalyst prepared by mixing an alkali or alkali liquor with an aqueous solution of manganese and magnesium ions to obtain a co-precipitation of the manganese salt and magnesium salt based on the added alkali, of which the coprecipitate is filtered, water-washed, dried, ground and molded to the desired shape by adding water thereto, and finally calcined at 25020 C. -600° C. for 1-4 hours to form a catalyst containing a mixture of magnesium oxide and manganese oxide wherein the atomic ratio of Mn:Mg is ranging from 1:100 to 100:100.

The calcined catalyst has a surface area of at least 20 m$^z$/g, preferably ranging from 80-300 m$^z$/g. The catalyst shape is not limited in this invention and can be formed as a sphere, a cylinder, a ring, a semi-annular shape or any other shapes, or even formed as particle having a size of 10 μm (or up) suitable for use in a fluidized bed.

The aforesaid aqueous solution of manganese and magnesium ions is prepared by dissolving a water-soluble manganese salt and magnesium salt in the water. The available magnesium and manganese salts are salts of chlorate, nitrate, sulfate and acetate. The manganese salt and magnesium salt can be simultaneously or subsequently dissolved in a water solution for making the aforesaid aqueous solution of manganese and magnesium ions.

The quantity and concentration of the alkali liquor should be enough to thoroughly precipitate the Mg/Mn ions. The suitable alkali liquid may be selected from: ammonia water, sodium hydroxide, potassium hydroxide, sodium carbonate, sodium bicarbonate, potassium carbonate and potassium bicarbonate. Generally speaking, the alkali liquid is added to start the precipitation when the pH value of the mixing solution is 8.0 and the pH of the final precipitated solution is about 9.3 or up. The aforesaid precipitate of magnesium or manganese salt has a salt radical correspondingly derived from a radical of the alkali as added. For instance, a potassium hydroxide is added to form precipitate of magnesium hydroxide or manganese hydroxide, and a carbonate of alkali metal is added to possibly form a precipitate of carbonate or hydroxide.

The prepared catalyst when impregnated with a thin layer of oxide of alkali metal (trace) may prolong its service life. The catalyst as previously prepared is impregnated in an aqueous solution of alkali metal salt or hydroxide and then dried and calcined at a high temperature ranging from 250°-600° C. for 1 - 3 hours to thermally decompose into an alkali metal oxide. The available alkali metal salts may be selected from: nitrate, carbonate, acetate, oxalate, etc. The quantity of alkali metal oxide added to the catalyst should be less than 0.5% by weight and preferably ranging from 0.0001-0.1 wt. % based on weight of the catalyst.

In preparing an ortho-alkylated phenol by catalytically reacting phenol and alcohol at a high temperature, the process as disclosed in U.S. Pat. Nos. 3,446,856 and 3,974,229 may serve as a reference in the present invention. In the catalytic reaction of this invention, an alkyl alcohol may be selected from a saturated alkyl alcohol, such as: methanol, ethanol, propanol, cyclohexanol and an alkyl alcohol having more than ten carbon atoms and may preferably be a methanol or an alkyl alcohol having carbon atoms not more than six; and a phenol compound may be selected from a phenol having an ortho position not being substituted and having a general formula:

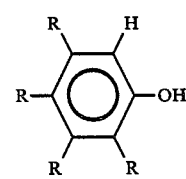

wherein R is a monovalent substituent selected from the gronp consisting of: hydrogen, C1 –C12 alkyl, phenyl, or C1 –C12 alkyl substituted phenyl.

Preferably, a vapor methanol and phenol or ortho-cresol is reacted on a catalyst bed at 300°–550° C. (preferably at 380 500°C.) to produce ortho-cresol or 2,6-dimethyl phenol (2,6 DMP) in this invention.

In conducting the catalytic reaction of the present invention, at least one mole of alkyl alcohol and preferably 1 4 moles of alcohol with respect to one mole of phenol is used to produce an ortho-alkylated phenol with a high yield. By adding water of 20 wt % based on the weight of the feed materials may prolong the catalyst life, The produce effluent passing through the catalytic bed may be cooled, separated and purified by crystallization, distillation or other conventional methods.

When the catalyst is deactivated after being used for a period, the deactivated catalyst can be regenerated by passing an air or steam stream at 300°–60020 C. through the catalyst bed for removing carbon accumulated on the catalyst surface.

Any conventional catalytic reactor such as a fixed bed or fluidized bed reactor, an isothermal or adiabatic reactor may be optionally chosen in this invention. The reaction is conducted under normal pressure, reduced pressure or even up to 30 kg/cm.

The present invention can be further described in the following examples, which examples are given by way of illustration and not by way of limitation. In all of the examples, the percentages are by moles, unless otherwise stated.

EXAMPLE 1

A. Preparation of catalyst 500 g Mg(NO$_3$)$_2$· 6H$_2$O and 20 g Mn(NO$_3$)$_2$· 6H$_2$O are added into 500 ml deionized water to form a mixing water solution which is then agitated to be thoroughly soluble. A 28% ammonia water is slowly added into the aforesaid water solution until a pH 10.3 is present in the solution. A coprecipitate of hydroxide is formed and the solution is continuously agitated for 1 hour. The coprecipitate is filtered off from the solution and washed by deionized water, and then dried at 120° C. for 1–2 hours. The dried product is ground and molded by blending water therewith to form cylindrical catalyst each having a size of 4 mm $\phi \times 6$ mmL which is then calcined at 350° C. for 3 hours to activate the catalyst having an atomic ratio of 100:5 for Mg:Mn.

B. Preparation of ortho - cresol

A catalyst prepared as above mentioned of 30 g is added into a reactor which is maintained at a fixed temperature by an electric oven and a feed composition of phenol: methanol:water of 1:6:1 (mole ratio) is fed into the reactor at a rate of 30 ml/hr for conducting the catalytic alkylation reaction. The product is collected, cooled and analysed by gas chromatography to obtain a reaction result as shown in the following Table 1, Test 1.

Contrast Example 1

By repeating the process as disclosed in U.S. Pat. Nos. 3,972,836 and 3,974,229 (run 3a of Example 3) to prepare a catalyst containing particles of magnesium oxide and Mn$_2$O$_3$, calcined at 350° C. in 3 hours, a final product is obtained and analysed in the following Table 1, Test 1a.

TABLE 1

| Catalyst | Test 1 | Test 1a |
|---|---|---|
| Mn/Mg atomi ratio | 5/100 | 5/100 |
| Preparation method | Co-precipitation | Physical blending |
| Reaction conditions | | |
| Pressure | Normal pressure | Normal pressure |
| WHSV (hr $^{-1}$)$^{(i)}$ | 0.9 | 0.9 |
| Time on stream (hr) | 51 629 1181 | 27 |
| Temperature (°C.) | 445 445 480 | 480 |
| Results | | |
| Conversion of phenol (mole %)$^{(ii)}$ | 9.7 99.6 99.0 | 97.9 |
| Products distribution (mole %)$^{(iii)}$ | | |
| O - cresol | 9.2 13.6 13.5 | 31.4 |
| 2,6 - DMP | 83.8 83.6 84.3 | 66.5 |
| Ortho-selectivity$^{(iv)}$ (mole %) | 93.0 97.2 97.8 | 97.9 |
| yield of 2.6 - DMP (mole %) | 83.5 83.2 83.4 | 64.9 |

Note:
$^{(i)}$WHSV is a liquid weight hourly space velocity, defined as a liquid weight of the reactants passing through a unit weight of catalyst per hour.
$^{(ii)}$The phenol conversion is the moles of phenol actually reacted in the reaction among the reactants, per mole of phenol.
$^{(iii)}$The products distribution is mole ratio of each individual phenolic product based on the total moles of all phenol products.
$^{(iv)}$The ortho-selectivity is defined as a mole ratio of O - cresol and 2,6 - DMP based on all of the phenolic products.
$^{(v)}$The yield of 2,6 - DMP is defined as the moles of 2,6 - DMP produced from each mole of phenol in the reactants.

From the abovementioned analysis of Table 1, the preparation for making ortho-alkylated phenol in the presence of a catalyst of this invention prepared by coprecipitation may reduce its initial reaction temperature for 35° C. less than that of Van Sorge's process by using a catalyst prepared by physical blending of MgO/MnO. Meanwhile, the present invention may have a higher phenol conversion and higher yield of 2,6 - DMP than that of the prior art, thereby proving that a catalyst prepared by coprecipitation as disclosed in this invention may have a higher catalyst activity than that of the prior art.

The preparation from phenol to ortho-cresol and from O-cresol to 2,6 - dimethyl phenol is a two-step continuous reaction. Much final product (2,6 - DMP) of the second step produced may express a better activity of the catalyst in accordance with this invention. From the test result, a higher yield of final product 2,6 - DMP is maintained above 80% for a long period of 1181 hours. However, the yield of 2,6 - DMP as taught by Van Sorge's U.S. Pat. No. 3,974,229 can not reach 80% (up) yield of 2,6 - DMP at 480° C. of reaction temperature. As shown in Van Sorge's example 3 (run 3a), the 2,6 - DMP distribution at 480° C. for 400 hours of reaction time is only 50.2 wt %. Comparatively, this invention has a 2,6 - DMP distribution of 83.8% and 83.6% respectively for a time of 51 and 629 hours and maintains a 2,6 - DMP yield of 83,5 and 83.2 without degradation for a time of 51 and 629 hours, and still maintain a high yield even after 1181 hours of reaction time. Accordingly, this invention may have a better performance of catalyst, much improved over that as taught by Van Sorge's process.

EXAMPLE 2

By repeating the steps of Example 1 but changing the reaction condition for preparing the catalyst, such as: the choices of Mg, Mn salts, their proportion and concentrations, the selection of alkali and concentration thereof, precipitation methods or calcination temperature, etc. and by adjusting a feed composition of phenol:

methanol: water to be 1:6:1, the reaction conditions and results are given in Table 2.

The atomic ratio of Mn/Mg is 1/100 to 100/100. The desired catalyst can be obtained by selectively changing the metallic salts, alkali, the solution concentration and precipitation methods as shown in Table 2. The calcination of catalyst is operated at 250°-600° C., The catalytic reaction is performed at 380°-500° C., WSHV of 0.5 $hr^{-1}$ — 5.0 $hr^{-1}$, under a pressure of normal pressure to 30 kg/cm².

TABLE 2

| Run | 2 | 3 | 4 |
|---|---|---|---|
| Mn/Mg atomic ratio | 5/100 | 5/100[iii] | 5/100 |
| Mn Salt | $Mn(NO_3)_2.6H_2O$ | $Mn(NO_3)_2.6H_2O$ | $Mn(NO_3)_2.6H_2O$ |
| Mg salt | $Mg(NO_3)_2.6H_2O$ | $Mg(NO_3)_2.6H_2O$ | $Mg(NO_3)_2.6H_2O$ |
| Concentration of metal salt solution | 51 | 51 | 51 |
| Alkali | $NH_4OH$ | $NH_4OH$ | $NH_4OH$ |
| Concentration of Alkali solution (wt %) | 28 | 28 | 28 |
| Precipitation Method[i] | A | C | A |
| Calcination temperature (°C.) | 250 | 350 | 600 |
| Reaction condition |  |  |  |
| Temperature (°C.) | 430 | 420 | 460 |
| Pressure (kg/cm²) | 9 | 15 | 9 |
| WHSV ($hr^{-1}$) | 2.4 | 4.0 | 2.4 |
| Result |  |  |  |
| Phenol conversion (mole %) | 99.4 | 88.0 | 86.7 |
| 2.6 - DMP selectivity (mole %)[ii] | 83.2 | 73.1 | 51.8 |
| 2.6 - DMP yield (mole %) | 82.7 | 72.0 | 45.0 |

| Run | 5 | 6 | 7 |
|---|---|---|---|
| Mn/Mg atomic ratio | 1/100 | 20/100 | 100/100 |
| Mn Salt | $MnCl_2.4H_2O$ | $Mn(CH_3COO)_2.4H_2O$ | $MnSO_4.H_2O$ |
| Mg salt | $MgCl_2.6H_2O$ | $Mg(CH_3COO)_2.4H_2O$ | $MgSO_4.7H_2O$ |
| Concentration of metal salt solution | 39 | 22 | 10 |
| Alkali | $NH_4OH$ | $NH_4OH$ | $NH_4OH$ |
| Concentration of Alkali solution (wt %) | 33 | 33 | 12 |
| Precipitation Method[i] | B | A | A |
| Calcination temperature (°C.) | 500 | 500 | 500 |
| Reaction condition |  |  |  |
| Temperature (°C.) | 480 | 460 | 450 |
| Pressure (kg/cm²) | 9 | 9 | 9 |
| WHSV ($hr^{-1}$) | 2.4 | 2.4 | 2.4 |
| Result |  |  |  |
| Phenol conversion (mole %) | 96.7 | 100 | 99.6 |
| 2.6 - DMP selectivity (mole %)[ii] | 71.7 | 82.8 | 72.2 |
| 2.6 - DMP yield (mole %) | 69.3 | 82.8 | 71.9 |

| Run | 8 | 9 |
|---|---|---|
| Mn/Mg atomic ratio | 5/100 | 5/100 |
| Mn Salt | $Mn(NO_3)_2.6H_2O$ | $Mn(NO_3)_2.6H_2O$ |
| Mg salt | $M(NO_3)_2.6H_2O$ | $Mg(NO_3)_2.6H_2O$ |
| Concentration of metal salt solution (wt %) | 59 | 59 |
| Alkali | NaOH | $Na_2CO_3$ |
| Concentration of Alkali solution (wt %) | 40 | 10 |
| Precipitation Method[i] | A | A |
| Calcination temperature (°C.) | 350 | 380 |
| Reaction condition |  |  |
| Temperature (°C.) | 430 | 430 |
| Pressure (kg/cm²) | normal pressure | normal pressure |
| WHSV ($hr^{-1}$) | 0.9 | 0.9 |
| Result |  |  |
| Phenol conversion (mole %) | 99.4 | 100 |
| 2.6 - DMP selectivity (mole %)[ii] | 73.3 | 79.9 |
| 2.6 - DMP yield |  |  |

TABLE 2-continued

| | | |
|---|---|---|
| (mole %) | 72.8 | 79.9 |

Note:
[i] Precipitation method:
A: Alkali is added into a metal salt solution for their mixing;
B: Metal salt solution is added into alkali solution;
C: Alkali solution and metal salt solution are simultaneously added.
[ii] 2,6 - DMP selectivity is defined as the moles of 2,6 - DMP produced per mole of plenol reacted.
[iii] Catalyst includes 0.05 wt % $K_2O$.

EXAMPLE 3

The process of example 1 is repeated to prepare much catalyst of which Mn/Mg is 5/100. 60 g catalyst is impregnated in a solution dissolved with 1.3 mg $KNO_3$ for 1 hour and slowly dried at 60° C. and then calcined at 350° C. for 3 hours to produce a catalyst having 0.001 wt % $K_2O$, By charging a feed composition of phenol: methanol: water of 1:6:1 into a reactor containing the $K_2O$ impregnated catalyst for performing the alkylation reaction under 9 Kg/cm$^2$, WHSV 2.4 hr$^{-1}$, of which the reaction condition and result are summarized in Table 3, Run 10; a contrast test is performed without containing of $K_2O$ of which the reaction condition and result are shown in Run 11.

TABLE 3

| Run | 10 | 11 |
|---|---|---|
| Mn/M atomic ratio | 5/100 | 5/100 |
| $K_2O$ (wt %) | 0.001 | 0 |
| Reaction temperature (°C.) | 440 | 430 |
| Result | | |
| Phenol conversion (%) | 99.2 | 100 |
| 2,6 - DMP yield (%) | 83.7 | 75.6 |
| Life (hr) | 2210 | 823 |

Note:
The life is defined as a total reaction time from starting the reaction till the reaction conducting at 180° C. to obtain a 2,6 - DMP yield of more than 70%.

From Table 3, it is quite clear that the life can be prolonged by using a catalyst consisting of $K_2O$. Even trace of alkali metal oxide is added, its life can be 2.7 times of that without containing alkali metal oxide.

EXAMPLE 4

Preparing a catalyst by using the method of Example 3, consisting of $Li_2O$ 0.1 wt %, $K_2O$ 0.05 wt % and $Cs_2O$ 0.1 wt %. The reaction condition and result are shown in Table 4, from which the catalyst containing 0.1 wt % of alkali metal oxide may reveal a better result.

TABLE 4

| Run | 12 | 13 | 14 |
|---|---|---|---|
| Mn/Mg atomic ratio | 5/100 | 5/100 | 5/100 |
| Alkali metal oxide | Li O | K O | Cs O |
| Alkali metal oxide (wt %) | 0.1 | 0.05 | 0.1 |
| Reaction condition | | | |
| Pressure (Kg/Cm$^2$) | 10 | 10 | 10 |
| WHSV (hr$^{-1}$) | 0.9 | 0.9 | 0.9 |
| Temperature (°C.) | 435 | 425 | 445 |
| Result | | | |
| Reaction time (hr) | 97  510 | 77  1345 | 386 |
| Phenol conversion (mole %) | 98.3  99.4 | 98.9  99.4 | 99.3 |
| 2.6 - DMP (mole %) | 66.5  79.8 | 68.5  70.2 | 65.1 |

EXAMPLE 5

The process of Example 1 is repeated, but the solutions of Mg and Mn salts are slowly added into the ammonia water to obtain a catalyst by precipitation. A feed composition of phenol: methanol: water of 1:6:1 is fed into the reactor for catalytic reaction under 9 Kg/cm$^2$, WHSV 2,4 hr$^{-1}$, of which the reaction condition and result are shown in Table 5, Run 15. Comparatively, a catalyst prepared by Example 1 is used and a feed composition of phenol: methanol: water of 1:9:3 is fed and reacted under normal pressure, WHSV 2.7 hr-1, as shown in Run 16.

TABLE 5

| Run | 15 | 16 | |
|---|---|---|---|
| Mn/Mg atomic ratio | 5/100 | 5/100 | |
| Phenol:methanol:water | | | |
| (mole ratio) | 1:6:1 | 1:9:3 | |
| Pressure (Kg/cm$^2$) | 9 | normal pressure | |
| WHSV (hr$^{-1}$) | 2.4 | 2.7 | |
| Temperature (°C.) | 435 | 450 | 470 |
| Result | | | |
| Phenol conversion (mole %) | 79.6 | 50.6 | 90 |
| O - Cresol selectivity | | | |
| (mole %) | 80.2 | 86.0 | 53 |
| 2.6 - DMP selectivity | 18.3 | 11.6 | 44 |
| (mole %) | | | |
| Ortho-methylation selectivity | | | |
| (mole %) | 98.5 | 98.3 | 98 |

Note:
The ortho-methylation selectivity is defined as the moles of o-cresol and 2,6 - DMP in the products per mole of phenol converted in the reaction, i.e., the mole ratio of the desired products to the total products.

From Table 5, the ortho-methylation of phenol can be selectively reacted to produce o-cresol or 2,6 - DMP. Even the feed moles of methanol is as high as 9 times of the phenol, the ortho-alkylation selectivity may even reach more than 98%.

EXAMPLE 6

By using the catalyst as prepared by Example 1, 2,6 - DMP is prepared from a feed composition of o-cresol, methanol and water. During the proceeding of the reaction, the mole ratio of the feed composition is adjusted several times, of which the reaction condition and result are shown in Table 6.

TABLE 6

| | Run 17 | | |
|---|---|---|---|
| Reaction condition | | | |
| Reaction time (hr) | 175 | 1345 | 1614 |
| Feed mole ratio | | | |
| O - cresol:phenol: | 1:0: | 0.9:0.1: | 0.5:0.5 |
| MeOH:H O | 4.5:2 | 4.5:2 | 5.25:1 |
| Temperature (°C.) | 440 | 450 | 460 |
| WHSV (hr$^{-1}$) | 1.8 | 1.8 | 1.4 |
| Result | | | |
| 2.6 - DMP yield (mole %) | 89.0 | 83.0 | 79.1 |

From Table 6, a mixture of o-cresol and phenol may produce 2,6 - DMP of high yield. The unreacted phenol in the products is less than 1 mole %. If the water quantity is changed in the reaction, a high yield of 2,6 - DMP may also be obtained.

From the above examples and illustration, it is understood that a high yield of ortho-alkylated phenol products, longer catalyst life and higher catalyst activity in accordance with the present invention can be obtained, superior to Van Sorge's prior art.

We claim:

1. A process for preparing an ortho-alkylated phenol by a vapor phase catalytic reaction at 200°-500° C. by reacting a vapor phenol compound selected from phenol, ortho-cresol and a mixture of phenol mixed with ortho-cresol and a vapor alcohol selected from methanol cyclohexanol or an alkyl alcohol having more than ten carbon atoms, in the presence of a catalyst containing magnesium oxide and maganese oxide, of which the catalyst is prepared by first forming a coprecipitate of magnesium and manganese salt, said coprecipitate being then filtered, water-washed and calcined at 250°-600° C. for 1-4 hours for forming the catalyst consisting of magnesium oxide and manganese oxide having an atomic ratio of Mg/Mn of 100:100 to 100:1, the improvement which comprises:

said coprecipitate of magnesium and manganese salt being prepared by treating an alkali in an aqueous solution having soluble magnesium ion and soluble manganese ion to obtain said coprecipitate of magnesium and manganese salt with respect to the alkali added.

2. A process according to claim 1, wherin said aqueous solution of magnesium and manganese ions is made by dissolving a water-soluble magnesium salt and manganese salt in the water; or made by mixing an aqueous solution of water-soluble magnesium salt and the other aqueous solution of water-soluble manganese salt.

3. A process according to claim 2, wherein the water-soluble magnesium salt is selected from the salts of: nitrate, halogenate, sulfate and acetate.

4. A process according to claim 2, wherein the water-soluble manganese salt is selected from the salts of: nitrate, halogenate, sulfate, and acetate.

5. A process according to claim 1, wherein the alkali is selected from: ammonia, sodium hydroxide, potassium hydroxide, sodium carbonate, potassium carbonate, sodium bicarbonate, and potassium bicarbonate.

6. A process according to claim 5, wherein said alkali further comprises an aqueous solution of said alkali.

7. A process according to claim 1, wherein the preparation of the catalyst further comprises impregnating the prepared catalyst in an aqueous solution of an alkali metal salt or alkali metal hydroxide, and then dried, calcined at 250°-600° C. for 1-3 hours to form a thin layer of alkali metal oxide on the surface of the catalyst.

8. A process according to claim 7, wherein said aqueous solution of alkali metal salt or hydroxide is an aqueous solution of an alkali metal salt of nitrate, carbonate, acetate or oxalate, or an aqueous solution of an alkali metal hydroxide.

9. A process for preparing an ortho-alkylated phenol by a vapor phase catalytic reaction at 200°-50020 C. by reacting a vapor phenol compound selected from phenol, orthocresol and a mixture of phenol mixed with ortho-cresol and a vapor alcohol selected from methanol cyclohexanol or an alkyl alcohol having more than ten carbon atoms, in the presence of a catalyst containing magnesium oxide and manganese oxide, of which the catalyst is prepared by first forming a coprecipitate of magnesium and manganese salt, said coprecipitate being then filtered, waterwashed, dried, ground, molded by blending water therewith to a desired shape and calcined at 250°-600° C. for 1-4 hours for forming the catalyst consisting of magnesium oxide and manganese oxide having an atomic ratio of Mg/Mn of 100:100 to 100:1, the improvement which comprises:

said coprecipitate of magnesium and manganese salt being prepared by treating an alkali in an aqueous solution having soluble magnesium ion and soluble manganese ion to obtain said coprecipitate of magnesium and manganese salt with respect to the alkali added.